United States Patent [19]

Brendle

[11] Patent Number: 5,620,943
[45] Date of Patent: Apr. 15, 1997

[54] PROCESS FOR IDENTIFYING A LOCATION TO WHICH A SUBSTANCE HAS BEEN APPLIED

[75] Inventor: Ralph N. Brendle, Spartanburg, S.C.

[73] Assignee: Milliken Research Corporation, Spartanburg, S.C.

[21] Appl. No.: 382,069

[22] Filed: Feb. 1, 1995

Related U.S. Application Data

[63] Continuation of Ser. No. 674,434, Mar. 22, 1991, Pat. No. 5,387,745, which is a continuation of Ser. No. 70,333, Jul. 6, 1987, abandoned, which is a continuation-in-part of Ser. No. 902,138, Sep. 3, 1986, abandoned, which is a continuation of Ser. No. 778,153, Sep. 16, 1985, abandoned, which is a continuation of Ser. No. 464,664, Feb. 7, 1983, abandoned.

[51] Int. Cl.$^6$ .............................. A01N 25/00; C05G 3/00
[52] U.S. Cl. ...................... 504/116; 71/DIG. 1; 514/772
[58] Field of Search ...................... 504/116; 71/DIG. 1; 514/772

[56] References Cited

U.S. PATENT DOCUMENTS

| | | | |
|---|---|---|---|
| 1,947,320 | 2/1934 | Truffaut | 167/22 |
| 3,083,089 | 3/1963 | Renner | 71/2.4 |
| 3,157,633 | 11/1964 | Kuhn | 260/200 |
| 3,461,201 | 8/1969 | Champion | 424/125 |
| 3,497,345 | 2/1970 | Duyfies | 71/105 |
| 3,864,114 | 2/1975 | Green | 71/3 |
| 3,873,689 | 3/1975 | Fransch et al. | 424/78 |
| 3,925,927 | 12/1975 | Linton | 47/1.5 |
| 3,927,044 | 12/1975 | Foster et al. | 260/394 |
| 4,167,510 | 9/1979 | Brendle | 260/174 |
| 4,400,320 | 8/1983 | Keller et al. | 260/158 |

*Primary Examiner*—S. Mark Clardy
*Attorney, Agent, or Firm*—Terry T. Moyer; Timothy J. Monahan

[57] ABSTRACT

A process is provided for identifying a location to which a substance has been applied, which comprises incorporating into said substance prior to its application to said location an alkyleneoxy substituted fugitive colorant ingredient in an amount sufficient to identify the location to which the substance is to be applied; and thereafter applying said substance to said location.

29 Claims, No Drawings

PROCESS FOR IDENTIFYING A LOCATION TO WHICH A SUBSTANCE HAS BEEN APPLIED

This is a continuation application of application Ser. No. 07/674,434, filed on Mar. 22, 1991, now U.S. Pat. No. 5,387,745, which in turn is a continuation of Ser. No. 07/070,333 filed Jul. 6, 1987, now abandoned, which in turn is a continuation-in-part of U.S. Ser. No. 06,902,138, filed Sep. 3, 1986, abandoned, which is a continuation of Ser. No. 06/778,153, filed Sep. 16, 1985 abandoned, which is a continuation of Ser. No. 06/464,664, filed Feb. 7, 1983, abandoned.

The present invention relates to a process for identifying a location to which a substance has been applied.

Frequently, when a substance is applied to a location it may be difficult during the application process by virtue of, for instance, the nature of the substance and/or the size and configuration of the location to determine where the substance has been applied and where it has not been applied. For instance, where a substance such as a fertilizer, pesticide, etc., is being applied to a land area, e.g., farmland, golf course, rights-of-way, woodlands, etc., the appearance of the area which has been treated may not be sufficiently altered from the surrounding non-treated areas for the operator to avoid either overlapping which may be costly or even damaging to the location or alternatively certain areas may go untreated entirely so that the desired result of the application effort is not achieved in that area.

Solutions for the problem which have been suggested have included the incorporation of certain non-fugitive or permanent dyes in the substance to be applied to identify the location to which the substance has been applied. In particular, it has been suggested, for instance, to incorporate certain non-fugitive or permanent dyes in pesticide compositions such as insecticides, fungicides, herbicides, etc. to identify the location to which the pesticide has been applied and to distinguish it in particular from those locations yet to be treated with the pesticide.

Unfortunately, there are numerous problems associated with such compositions containing permanent dyes. For instance, the dyes may be toxic or they may be incompatible with one or more ingredients of the composition. They may cause staining of workers' hands and clothing. Equipment may become stained. The permanent dyes which have been used typically are nonbiodegradable and, therefore, are subject to environmental objections such as, for instance, environmental objections associated with the contamination of streams and other bodies of water associated with "run-off" of toxic agricultural chemical water into those bodies of water. Further, and perhaps most importantly, it may be difficult to achieve a color that would be aesthetically acceptable from the viewpoint of the area being treated.

It has been found that the present invention may overcome the above difficulties associated with known processes involving, for instance, the use of substances containing permanent dyes. Thus, it may now be possible to identify locations to which substances have been applied without causing permanent staining of workers' clothes and hands, etc. It may further be possible to provide a process involving the use of a composition wherein the colorant component is compatible with the components of the composition to be applied, nontoxic, biodegradable and therefore nonharmful to the environment. In particular, it may be possible to provide a process employing marking colorants which are generally non-toxic to aquatic life especially fish when the colorant comes into contact with a given body of water as a result of "run-off" from the land areas in the watershed of that body of water. In addition, it may be possible according to the process to achieve identification by coloration of locations to which a substance has been applied in such a way that the color can be shaded to match the aesthetics of the surrounding environment. This result may be especially desirable where the location to be treated is a turf grass such as that used in lawns, golf courses, athletic fields and the like.

According to the present invention a process is provided for identifying a location to which a substance has been applied, which comprises incorporating into said substance prior to its application to said location an alkyleneoxy-substituted fugitive colorant ingredient in an amount sufficient to identify the location to which the substance is to be applied; and thereafter applying said substance to said location.

Locations to which a particular substance may be applied according to the present invention include virtually anything to which may be applied a given solid and/or liquid substance to typically achieve a desirable effect. Locations may include surface portions of animate or inanimate objects, e.g., naturally occurring objects, man-made objects and the like. According to a preferred embodiment of the invention, the location may be a given land area, e.g., agricultural land such as grazing land, crop land and the like; turf-covered land areas, e.g., lawns, golf courses, athletic fields, etc., and even other land areas such as forests, and highway and utility rights of way. An even more preferred location may be land area within the watershed of a given body of water where run-off from the land to the body of water is likely to occur. Other locations which are contemplated by the invention include man-made surfaces, e.g., building surfaces such as foundations, paved highways, parking lots and the like.

Substances which may be applied to a location according to the process of the present invention include any of a wide variety of liquid phase and/or solid phase substances that may achieve a desired effect when applied to the location. In general the substance may be characterized in that the location to which the substance has been applied is not substantially changed in appearance immediately upon application of the substance to the location. Thus it typically may be difficult or at least inconvenient for a person who is applying the substance by mechanical means or even by hand to determine where the substance has been applied to avoid overlapping or even indeed leaving certain areas entirely untreated. Overlapping may be costly depending upon the cost of the substance itself. Alternatively if certain areas are left untreated by the substance the desired effect to be achieved by the substance may not come about.

In addition because of the presence of the color it has been found that misapplication of the substance to areas which are not to be treated is more easily avoidable.

Substances which may be included within the scope of the present invention according to a preferred embodiment include, for instance, chemical compositions especially agricultural chemicals in solid and/or liquid phase, e.g., pesticide compositions especially fungicides, herbicides and insecticides; fertilizers (solid phase and/or liquid phase). Examples of other types of chemicals not typically considered to be agricultural chemicals include sand or salt mixtures which may be applied to highways, sidewalks, etc. to alleviate hazardous conditions on snow and ice covered areas.

The amount of substance applied will be that amount that is conventionally applied to achieve a desired effect.

Alkyleneoxy-substituted fugitive colorant compounds within the scope of the present process invention include a wide variety of fugitive colorants of the type which have, for instance, often been used to color code textiles during production and/or finishing operations to identify certain synthetic or natural fibers. Such fugitive colorants may be water fugitive, solvent fugitive or both water and solvent fugitive, although water fugitive colorants may be preferred according to the present invention, especially when the location may be an exterior location so that natural rainfall will wash away the initial coloration effect, thereby returning the location to its natural appearance. Colorants containing one or more polyethyleneoxy groups wherein the polyethyleneoxy group contains at least 2 repeating ethyleneoxy units in the molecule are generally considered water fugitive colorants; whereas colorants containing one or more propyleneoxy groups having similar repeating propyleneoxy units in the molecule are considered solvent fugitive.

Fugitive colorants which may be employed according to the present invention include the polyethylene oxide colorants described in U.S. Pat. No. 3,157,663 (incorporated by reference). Such colorants are a combination of a dyestuff radical and one or more polyethyleneoxy groups. Dyestuff radicals disclosed in the patent include nitroso, nitro, azo, diphenylmethane, triphenylmethane, xanthene, acridine, methine, thiazole, indamine, azine, oxazine, or anthraquinone radicals. Preferably, such radicals are attached to the polymeric constituents of the colorant compositions by an amino nitrogen.

Another type of fugitive colorant which may be employed according to the present invention includes the alkaline-stable fugitive colorant of the triphenylmethane type as described in U.S. Pat. No. 3,927,044 (incorporated by reference).

Yet another category of fugitive colorants which may be employed in the process of the present invention are the ester capped alkyleneoxy fugitive colorants disclosed in U.S. Pat. No. 4,167,510 (incorporated by reference). Such fugitive colorants comprise an organic dyestuff molecule having from 1 to 5 capped alkyleneoxy units wherein the total alkyleneoxy capped units in the molecule are from 2 to about 300. The alkylene moiety of the alkyleneoxy units contains from about 2 to 4 carbon atoms and the colorants of the invention can be made water and/or organic solvent soluble depending upon the particular capping moiety employed, the presence or absence of at least one ionic group and the total number of alkyleneoxy units present in the colorant molecule. The solubility, and thus the fugitivity of the colorants may be achieved irrespective of whether the relatively large dyestuff molecule is hydrophobic or hydrophilic.

Still another category of fugitive colorants which may be employed according to the present invention includes those disclosed in copending U.S. Pat. No. 4,400,320, filed Jul. 13, 1981, entitled ALKYLENEOXY FUGITIVE TINTS AND PROCESS FOR PREPARING SAME, Keller et al (incorporated by reference). Such colorants may be characterized by the formula:

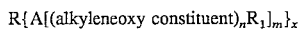

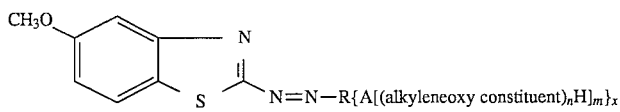

wherein R is selected from meta-toluidene, meta-amino phenol, aniline or dimethoxy aniline; A is selected from N,O,S or $CO_2$; the alkylene group of the alkyleneoxy constituent contains from 2 to about 4 carbon atoms; n is an integer of from 2 to about 300; m is 1 when A is O, S, or $CO_2$, and 2 when A is N; x is an integer of from 1 to about 5; and the product of n.m.x is from 2 to about 400.

According to a preferred embodiment the colorants of the present invention may be characterized as follows:

$$R\{A[(\text{alkyleneoxy constituent})_n R_1]_m\}_x$$

wherein R—A is an organic dyestuff molecule, A is a linking moiety in said organic dyestuff molecule selected from the group consisting of N, O, S or $CO_2$, the alkylene moiety of the alkyleneoxy constituent contains from 2 to about 4 carbon atoms, n is an integer of from 2 to about 300, m is 1 when A is O, S, $CO_2$ and 2 when A is N, x is an integer of from 1 to 5, and the product of n times×times m (n.m.x) is from 2 to about 300, and $R_1$ is a member of the group consisting of

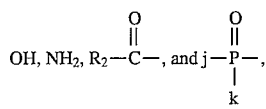

and sulfonates and sulfates of each of the members of said group, wherein $R_2$ is H, OH, an alkyl radical containing up to about 20 carbon atoms or alkyl substituted carbonyl radical containing up to about 20 carbon atoms, j and k are OH, OM or $OR_3$ wherein M is a cation moiety of an alkali metal, an alkaline earth metal or ammonium, and $R_3$ is an alkyl radical containing up to about 20 carbon atoms.

The term water soluble and/or fugitive as used herein is to be understood to mean that the colorant is substantially soluble in water and can be substantially removed by washing the location to which the substance containing the colorant has been applied with water. A typical example of washing operation would certainly include subjecting the location to rainwater, snow, etc. whereby the colorant may be removed. The term "water and organic solvent soluble and/or fugitive" is to be understood that the colorant is substantially soluble in water or an organic solvent and can be removed by washing the location with water or an organic solvent. Organic solvents which may be employed to treat the location are well-known in the art and include hydrocarbons, such as mineral oil, and organic solvents such as perchloroethylene, carbon tetrachloride and the like.

The amount of alkyleneoxy-substituted fugitive colorant employed according to the process, that is the amount provided in association with the particular substance, will vary greatly depending upon the quantity of substance to be applied to a given area, the nature of the substance itself, the location to which the substance is to be applied and possibly other factors. In general the colorant will be employed in association with the substance in an amount sufficient to visually identify the area to which the substance has been applied. Of course the colorant may be employed in larger concentrations, for instance, in those applications where temporary coloration may be appropriate or desirable. In general upper levels of the concentration range for the colorant may be discouraged not by any performance disadvantages but rather by cost considerations. The actual amount of colorant employed may typically be at least about 0.2 ounce of colorant per 1000 square feet of location area to be applied. A preferred amount may be at least about 2.0 ounces.

Preparation of the alkyleneoxy-substituted fugitive colorants is quite conventional and a wide variety of preparation procedures are generally described and exemplified in the patents referred to above which have been incorporated herein by reference. In general the colorants may be prepared by converting a dyestuff intermediate into a corresponding alkylene oxide containing compound, capping the alkylene oxide containing compound if desired, and thereafter employing the resulting alkylene oxide containing intermediate to react with a compound having a chromophoric group in the molecule to produce the desired fugitive tint composition. The method of producing the dyestuff intermediate containing the alkylene oxide constituent can be any suitable manner such as disclosed in U.S. Pat. No. 3,157,633 or 3,927,044.

The invention may be further understood by reference to the following examples which are not to be construed as limiting the scope of the present invention.

PREPARATION I

One mole (181 grams) of N,N-di(hydroxyethyl)aniline in a flask equipped with stirrer, thermometer and gas inlet tube near the bottom and a gas outlet tube near the top of the flask, was heated to 140° C. under nitrogen. About 200 mg. of sodium was added as catalyst. Ethylene oxide was bubbled into the molten, vigorously stirred material at a rate such that a slight amount of gas escaped from the outlet tube. The ethylene oxide addition was continued, with cooling to maintain the temperature between about 140°–160° C., until about 18 moles (792.9 g) of ethylene oxide was reacted, thus producing N,N-di(hydroxyethylpolyethyleneoxy)-aniline containing a total of about 20 ethyleneoxy groups.

PREPARATION II

One hundred two and two-tenths grams (0.523 mole) of N,N-dihydroxyethyl-m-toluidine was placed in a flask equipped with a stirrer, thermometer and gas inlet and outlet tubes. The air therein was replaced by nitrogen and the material was heated to about 140° C. About 200 mg. of sodium was added as a catalyst. Ethylene oxide was then bubbled into the vigorously stirred, molten material at a rate such that a slight amount of gas escaped from the outlet tube and until the reaction mixture had increased in weight to about 540 g. About 18 molar equivalents of ethylene oxide had thus being added to the starting material to produce the compound

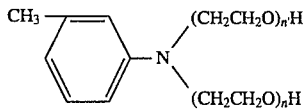

wherein n and n' each are about 10.

EXAMPLE I

Thirty grams (0.111 mole) of aniline—2,5 disulfonic acid were dissolved in 70 g of water, cooled to 5°–10° C. Sodium nitrite solution (which was produced by dissolving 9 g (0.13 moles) of sodium nitrite in 50 g of water) was added slowly. A pH of 2.5 or below was maintained with hydrochloric acid during sodium nitrite addition. One hundred and twenty-four grams (0.128 moles) of the compound from Preparation I was added slowly. After all the diazonium salt reacted (about 2 hours) the solution was made slightly alkaline with sodium hydroxide and sodium bicarbonate. A solution of a yellow colorant was obtained.

EXAMPLE II

A mixture of 500 g (0.534 mole) of the polyethylene oxy compound of Preparation I, 50 g (0.240 moles) of 0 formyl benzene sulfonic acid mono sodium salt and 50 g of hydrochloric acid with 10 grams urea was refluxed at a temperature of between 110°–120° C. for 6 hours. A mixture of 52 g (0.535 mole) of hydrogen peroxide and 52 g of water was added in one portion to the reaction mixture at 100°–105° C. whereupon the mixture was stirred an additional 30 minutes. The mixture was neutralized to neutral pH with sodium hydroxide and sodium bicarbonate. A solution of a blue colorant was obtained.

EXAMPLE III

Eleven and three-tenths grams (0.035 mole) of 1,8 naphtholamine—3-6 disulfonic acid was added to a solution of 80 g of water and 7 g of hydrochloric acid at 8°–10° C. Two and four tenths grams (0.035 mole) of sodium nitrite was dissolved in 15 g of water and slowly added to a solution of 1,8 naphtholamine—3-6 disulfonic acid, water and acid while the pH was maintained below 3.0. This formed the diazonium of 1,8 naphtholamine—3-6 disulfonic acid.

Thirty-five grams (0.038 mole) of Preparation II was mixed with 40 g of water and cooled to 5°–10° C. in a different container. The pH of the mixture was lowered to 3.0 with hydrochloric acid.

The diazonium of 1,8 naphtholamine—3-6 disulfonic acid was added to a mixture of Preparation II and water. A solution of sodium acetate and water was added at a rate to maintain a pH of 3.8 until all diazo was reacted. The mixture was neutralized to neutral pH with sodium hydroxide and sodium bicarbonate. A solution of a red colorant was obtained.

EXAMPLE IV

In this example twenty pounds of 2.4 D Amine (a broadleaf weed control herbicide available from Gordon Corporation and sold under the trademark Trimec); 3.5 pounds of the blue colorant prepared according to Example II were mixed in 97.06 gallons of water. This mixture was sprayed by means of a Broyhill Spray applicator at the rate of one to two hundred gallons per acre on an area of turf-covered land. The pattern of application of the herbicide to the land was readily discernable; so that not only could any possible unwanted overspray or misplaced application be avoided, but also overlapping was avoided and uniform application was achieved.

EXAMPLE V

Two gallons of Round-Up, a non-selective herbicide available from Monsanto, and 3.5 pounds of the colorant prepared according to Example II were mixed with 97.56 gallons of water. The mixture was sprayed with a pressurized sprayer at a rate of one hundred gallons per acre depending upon the foliage to be treated. The pattern of spray application was readily observable, overlapping as well as misplaced application was avoided and uniform application, avoiding leaving certain areas untreated was minimized.

EXAMPLE VI

One gallon of Termide, a mixture of Chlordane and Heptachlor available from Forshaw Chemical Co. and eight ounces of the colorant prepared according to Example II were mixed with 98.94 gallons of water. This formulation was applied at a rate to obtain visually observable saturation of the treated area with a pressurized spray applicator to a cement building foundation as a pretreatment for termites. Again uniform application with little or no overlapping and missed areas was achieved.

EXAMPLE VII

Aquatic toxicity tests were conducted to compare toxicity of the colorants employed in the process of the present invention to prior art colorants commonly employed in agricultural compositions as location indicators; the test method employed was the method described in "Method for Acute Toxicity Tests with Fish, Macroinvertibrates, and Amphibians," Ecological Research Series, EPA-660/3-75-009, U.S. Environmental Protection Agency, Corwallis, Oreg. 1975.

All acute tests were conducted under static, aerated conditions with a single introduction of the test colorant. Blue gill sunfish, with a mean standard length of 4.5 cm. and a mean weight of 0.95 grams were selected from a population obtained from a commercial hatchery and acclimated to laboratory conditions for five weeks. The population was fed a commercial dry food preparation daily and zero mortality was experienced two weeks prior to testing.

Exposures were conducted in 5 gallon glass aquaria with the following concentrations:

| | | | |
|---|---|---|---|
| #1 | - Control | - | |
| #2 | - 1.0% V/V* | - | Blazon Blue[1] |
| #3 | - 0.5% V/V | - | Blazon Blue |
| #4 | - 2.0% V/V | - | Blazon Blue |
| #5 | - 1.0% V/V | - | Blazon Red[2] |
| #6 | - 0.5% V/V | - | Blazon Red |
| #7 | - 2.0% V/V | - | Blazon Red |
| #8 | - 1.0% V/V | - | Blazon Yellow[3] |
| #9 | - 0.5% V/V | - | Blazon Yellow |
| #10 | - 2.0% V/V | - | Blazon Yellow |
| #11 | - Control | - | |
| #12 | - 0.069% V/V | - | Agromark[4] |
| #13 | - 0.6% W/V** | - | Aurogreen[5] |
| #14 | - 0.006% V/V | - | Agromark |
| #15 | - 0.06% W/V | - | Aurogreen |

*V/V means volume to volume
**W/V means weight to volume

[1] The term Blazon Blue as used herein refers to a compound of the formula:

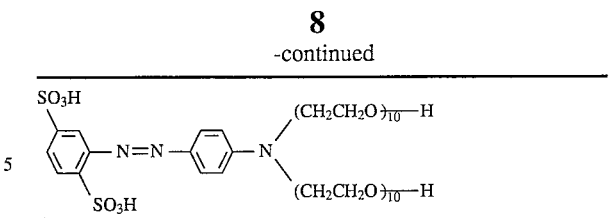

[2] The term Blazon Red as used herein refers to a compound of the formula:

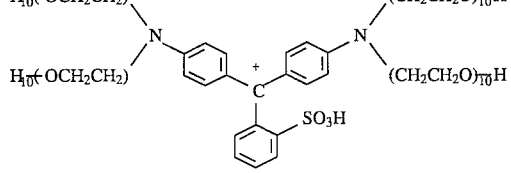

[3] The term Blazon Yellow as used herein refers to a compound of the formula:

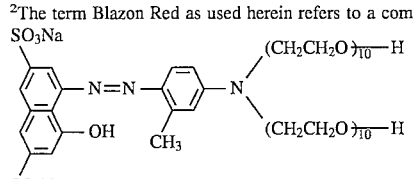

[4] Agromark is a triphenyl methane dye available from Amvac Chemical Corporation.
[5] Aurogreen is a blend of malachite green auramine and crystal violet available from Mallinckrodt, Inc.

Five fish were randomly added to each test aquaria to begin the test. Mortality counts and observations were recorded at two hour intervals for the first twenty-four hours and every twenty-four hours thereafter. Tests were run for ten day periods.

The results from the static acute tests are summarized as follows:

| TEST | TEST TIME | PERCENT LIVE |
|---|---|---|
| Control (#1 & #11) | 240 Hours | 100 |
| Blazon Blue (#2, #3, & #4) | 240 Hours | 100 |
| Blazon Red (#5, #6, & #7) | 240 Hours | 100 |
| Blazon Yellow (#8, #9, & #10) | 240 Hours | 100 |
| Aurogreen (#13) (0.6% W/V) | 2 Hours | 0 |
| Agromark (#12; .069% V/V) | 2 Hours | 0 |
| *Aurogreen (#15; .06% W/V) | 12 Hours | 0 |
| *Agromark (#14; .0069% V/V) | 2 Hours | 0 |

*These samples were taken from the original concentration and diluted 9:1 test water to sample.

These experiments indicate a marked difference in aquatic toxicity of alkyleneoxy substituted chromophore compounds and other competitive tints on blue gill sunfish.

What is claimed is:

1. In a process for identifying the location to which an agricultural chemical composition has been applied, an improvement comprising incorporating an alkyleneoxy substituted fugitive colorant in the composition, prior to its application to the location, in an amount sufficient to identify the location, wherein the colorant is selected from the group consisting of azo and triphenylmethane colorants.

2. The process of claim 1, wherein the location is selected from the group consisting of agricultural land, turf-covered land and forests.

3. The process of claim 2, wherein the alkyleneoxy substituted fugitive colorant is water soluble.

4. The process of claim 3, wherein the location is a golf course.

5. The process of claim 2, wherein the alkyleneoxy substituted fugitive colorant comprises a polyethyleneoxy group having at least two repeating ethyleneoxy units.

6. The process of claim 2, wherein the composition is a liquid and comprises an agricultural chemical selected from insecticides, fungicides, herbicides and fertilizers.

7. The process of claim 5, wherein the alkyleneoxy substituted fugitive colorants are water soluble.

8. The process of claim 7, wherein the alkyleneoxy substituted fugitive colorant is a triphenylmethane colorant.

9. A process for identifying the location to which an agricultural chemical composition has been applied comprising the steps of incorporating an alkyleneoxy substituted fugitive colorant in the composition, prior to its application to the location, in an amount sufficient to identify the location, wherein the colorant has the formula:

$$R(A((\text{alkyleneoxy constituent})_n R_1)_m)_x$$

wherein R—A is an organic dyestuff molecule, selected from the group consisting of azo and triphenylmethane molecules, A is a linking moiety in the organic dyestuff molecule selected from the group consisting of N, O, S and $CO_2$, the alkyleneoxy constituent comprises an alkylene moiety containing from 2 to about 4 carbon atoms, n is an integer of from 2 to about 300, m is 1 when A is O, S or $CO_2$ and 2 when A is N; x is an integer of from 1 to 5, and the product of n times×times m (n.m.x) is from 2 to about 300, and R, is selected from the group consisting of $$OH,\ NH_2,\ R_2-\overset{\overset{O}{\|}}{C}-,\ \text{and}\ j-\overset{\overset{O}{\|}}{\underset{\underset{k}{|}}{P}}-,$$

and sulfonates and sulfates of each of the members of the group, wherein R2 is H, OH, an alkyl radical containing up to about 20 carbon atoms or alkyl substituted carbonyl radical containing up to about 20 carbon atoms, j and k are OH, OM or OR3, wherein M is a cation moiety of an alkali metal, an alkaline earth metal or ammonium, and R3 is an alkyl radical containing up to about 20 carbon atoms; and thereafter applying the agricultural chemical composition to the location.

10. The process of claim 9, wherein the location is selected from the group consisting of agricultural land, turf-covered land and forests.

11. The process of claim 10, wherein the alkyleneoxy substituted fugitive colorant is water soluble.

12. The process of claim 11, wherein the location is a golf course.

13. The process of claim 10, wherein the alkyleneoxy substituted fugitive colorant comprises a polyethyleneoxy group having at least two repeating ethyleneoxy units.

14. The process of claim 10, wherein the composition is a liquid and comprises an agricultural chemical selected from insecticides, fungicides, herbicides and fertilizers.

15. The process of claim 14, wherein the alkyleneoxy substituted fugitive colorant is water soluble.

16. The process of claim 14, wherein the alkyleneoxy substituted fugitive colorant is a triphenylmethane colorant.

17. The process of claim 14, wherein the alkyleneoxy substituted fugitive colorant is selected from the group consisting of compounds of the formulas:

[structure: triphenylmethane colorant with [(alkyleneoxy constituent)$_n$R$_1$]$_m$A and A[(alkyloxy constituent)$_n$R$_1$]$_m$ substituents, and an SO$_3$H group]

[structure: naphthalene azo compound with SO$_3$Na, OH, SO$_3$Na, N=N, CH$_3$, and A[(alkyleneoxy constituent)$_n$R1]$_m$]

[structure: benzene-azo-benzene with SO$_3$H, SO$_3$H, N=N, and A[(alkyleneoxy constituent)$_n$R1]$_m$]

18. The process of claim 17, wherein the alkyleneoxy constituent is selected from the group consisting of ethyleneoxy and propyleneoxy units.

19. The process of claim 14, wherein A is N, and $R_1$ is OH.

20. An agricultural chemical composition for application to agricultural land, turf-covered land and forests, comprising:
  (a) an agricultural chemical selected from insecticides, fungicides, herbicides and fertilizers; and
  (b) a alkyleneoxy substituted fugitive colorant in an amount sufficient to visually identify an area to which the composition has been applied, wherein the colorant is selected from the group consisting of azo and triphenylmethane colorants.

21. The composition of claim 20, wherein the alkyleneoxy substituted fugitive colorant is water soluble.

22. The composition of claim 20, wherein the alkyleneoxy substituted fugitive colorant comprises a polyethyleneoxy group having at least two repeating ethyleneoxy units.

23. The composition of claim 20 wherein the alkyleneoxy substituted fugitive colorant has the formula:

$$R(A((\text{alkyleneoxy constituent})_n R_1)_m)_x$$

wherein R—A is an organic dyestuff molecule, A is a linking moiety in the organic dyestuff molecule selected from the group consisting of N, O, S and $CO_2$, the alkyleneoxy constituent comprises an alkylene moiety containing from 2 to about 4 carbon atoms, n is an integer of from 2 to about 300, m is 1 when A is O, S or $CO_2$ and 2 when A is N; x is an integer of from 1 to 5, and the product of n times×times m (n.m.x) is from 2 about 300, and $R_1$ is selected from the group consisting of $$OH;\ NH_2;\ R_2-\overset{\overset{O}{\|}}{C}-;\ \text{and}\ j-\overset{\overset{O}{\|}}{\underset{\underset{k}{|}}{P}}-,$$

and sulfonates and sulfates of each of the members of the group, wherein $R_2$ is H, OH, an alkyl radical containing up to about 20 carbon atoms or alkyl substituted carbonyl radical containing up to about 20 carbon atoms, j and k are OH, OM or OR$_3$, wherein M is a cation moiety of an alkali metal, an alkaline earth metal or ammonium, and R$_3$ is an alkyl radical containing up to about 20 carbon atoms.

24. The composition of claim 23, wherein the alkyleneoxy substituted fugitive colorant is a water soluble, triphenylmethane colorant.

25. The composition of claim 24, wherein the alkyleneoxy constituent is selected from the group consisting of ethyleneoxy and propyleneoxy units.

26. The composition of claim 23 wherein the alkyleneoxy substituted fugitive colorant is selected from the group consisting of compounds of the formulas:

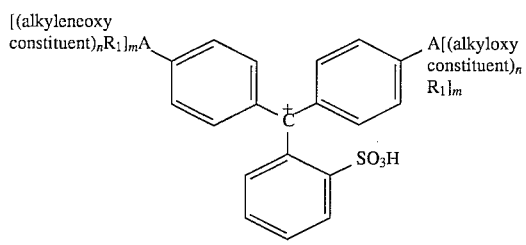
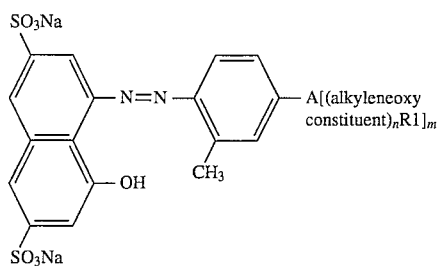
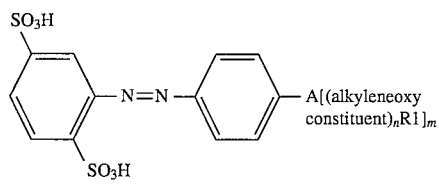
27. The composition of claim 28, wherein the alkyleneoxy constituent is seleted from the group consisting of ethyleneoxy and propyleneoxy units.
28. The composition of claim 27, wherein A is N, and $R_1$ is OH.
29. The composition of claim 20 wherein the agricultural chemical composition is in liquid phase.
* * * * *

UNITED STATES PATENT AND TRADEMARK OFFICE
CERTIFICATE OF CORRECTION

PATENT NO. : 5,620,943
DATED : April 15, 1997
INVENTOR(S) : Ralph N. Brendle

It is certified that error appears in the above-identified patent and that said Letters Patent is hereby corrected as shown below:

Column 9, Line 8 delete "R" and replace with $-R_1-$.

Column 9, Line 16 delete "R2" and replace with $-R_2-$.

Signed and Sealed this

Twentieth Day of April, 1999

Attest:

Q. TODD DICKINSON

Attesting Officer     *Acting Commissioner of Patents and Trademarks*